US009254104B2

(12) United States Patent
Judy et al.

(10) Patent No.: US 9,254,104 B2
(45) Date of Patent: Feb. 9, 2016

(54) SYSTEMS AND METHODS FOR REMOTE PATIENT MONITORING

(71) Applicants: John Judy, Glen Rock, NJ (US); Joe Petruzzelli, Paramus, NJ (US); Cadathur Rajagopalan, Dumont, NJ (US); Scott Eaton, Briarcliff Manor, NY (US); Sondra Kaufman, Ramsey, NJ (US); Susan Hebert, Lake Hiawatha, NJ (US)

(72) Inventors: John Judy, Glen Rock, NJ (US); Joe Petruzzelli, Paramus, NJ (US); Cadathur Rajagopalan, Dumont, NJ (US); Scott Eaton, Briarcliff Manor, NY (US); Sondra Kaufman, Ramsey, NJ (US); Susan Hebert, Lake Hiawatha, NJ (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 0 days.

(21) Appl. No.: 13/914,348

(22) Filed: Jun. 10, 2013

(65) Prior Publication Data

US 2013/0271283 A1 Oct. 17, 2013

(51) Int. Cl.
G08B 21/22 (2006.01)
A61B 5/00 (2006.01)
G06F 19/00 (2011.01)

(52) U.S. Cl.
CPC .............. A61B 5/742 (2013.01); A61B 5/7425 (2013.01); G06F 19/3418 (2013.01)

(58) Field of Classification Search
CPC ...................................................... A61B 5/742
USPC ............ 340/539.11, 539.12, 573.1; 600/300, 600/301, 483, 484, 485, 507; 702/19; 705/4; 710/3; 395.3, 913; 715/781, 791
See application file for complete search history.

(56) References Cited

U.S. PATENT DOCUMENTS

| | | | |
|---|---|---|---|
| 6,807,965 B1 | 10/2004 | Hickle | |
| 6,986,347 B2 | 1/2006 | Hickle | |
| 7,201,734 B2 | 4/2007 | Hickle | |
| 7,247,154 B2 | 7/2007 | Hickle | |
| 8,073,008 B2 * | 12/2011 | Mehta et al. | 370/468 |
| 8,095,692 B2 * | 1/2012 | Mehta et al. | 710/3 |
| 8,287,495 B2 * | 10/2012 | Michaud et al. | 604/151 |
| 8,359,338 B2 | 1/2013 | Butterfield et al. | |
| 8,475,386 B2 | 7/2013 | Parkin et al. | |
| 2006/0155589 A1 | 7/2006 | Lane et al. | |
| 2006/0200009 A1 | 9/2006 | Wekell et al. | |
| 2008/0108884 A1 | 5/2008 | Kiani | |
| 2009/0054743 A1 | 2/2009 | Stewart | |
| 2010/0261979 A1 * | 10/2010 | Kiani | 600/301 |
| 2010/0298718 A1 | 11/2010 | Gilham et al. | |
| 2011/0001605 A1 | 1/2011 | Kiani et al. | |
| 2011/0105854 A1 | 5/2011 | Kiani et al. | |
| 2011/0152770 A1 * | 6/2011 | DiPerna et al. | 604/151 |

(Continued)

Primary Examiner — Van Trieu

(57) ABSTRACT

A system includes a local patient monitor and a plurality of remote patient monitors. The local patient monitor may display a plurality of physiological parameters for a local patient. The local patient monitor may further display a remote monitoring interface with the local patient's physiological parameters. The remote monitoring interface may include a plurality of status icons respectively representing the plurality of remote patient monitors. In one embodiment, the local patient monitor receives alarm information from a first remote patient monitor indicating that one or more physiological parameters for a remote patient are outside of a determined range. The alarm information may include, for example, location information for the remote patient and an alarm condition indicated by the one or more physiological parameters. The local patient monitor may display the alarm information within the remote monitoring interface.

35 Claims, 8 Drawing Sheets

(56) References Cited

U.S. PATENT DOCUMENTS

2011/0152824 A1* 6/2011 DiPerna et al. ............... 604/500
2012/0030610 A1* 2/2012 DiPerna et al. ............... 715/773
2012/0075103 A1 3/2012 Powell et al.

* cited by examiner

SYSTEMS AND METHODS FOR REMOTE PATIENT MONITORING

TECHNICAL FIELD

This disclosure relates to patient monitors.

BRIEF SUMMARY

A system according to one embodiment includes a local patient monitor and a plurality of remote patient monitors. The local patient monitor may display a plurality of physiological parameters for a local patient. The local patient monitor may further display a remote monitoring interface with the local patient's physiological parameters. The remote monitoring interface may include a plurality of status icons respectively representing a remote monitoring status for each of the plurality of remote patient monitors.

In one embodiment, the local patient monitor receives alarm information from a first remote patient monitor indicating that one or more physiological parameters for a remote patient are outside of a determined range. The alarm information may include, for example, location information for the remote patient, as well as an alarm condition indicated by the one or more physiological parameters. The local patient monitor may display the alarm information within the remote monitoring interface.

Additional aspects will be apparent from the following detailed description, which proceeds with reference to the accompanying drawings.

DETAILED DESCRIPTION

Figure 1:
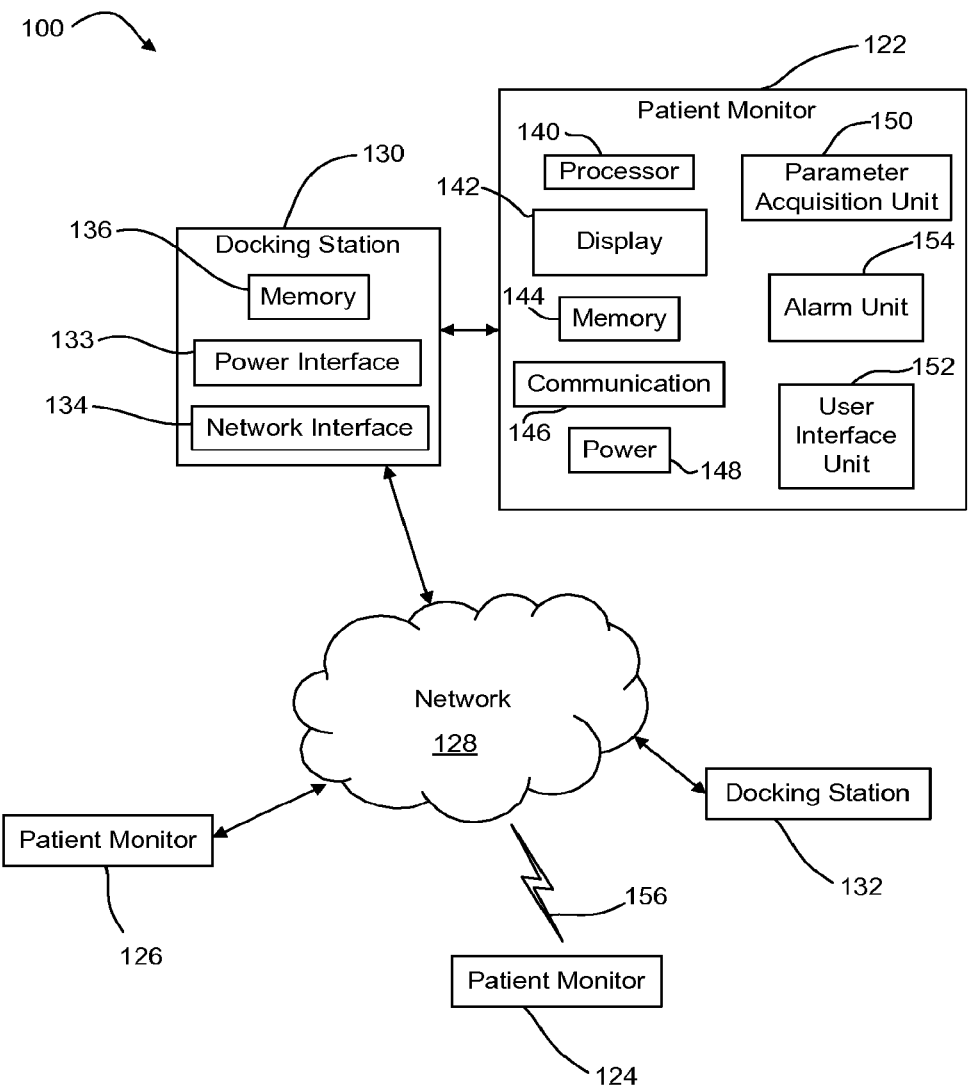
FIG. 1 is a block diagram of a patient monitoring system according to one embodiment.

Patient monitors are used to analyze and display physiological parameters obtained from sensors attached to a patient. The physiological parameters may include, for example, pulse, temperature, respiration, blood pressure, blood oxygen, electrocardiogram, etc. Often, patient monitors are configured to notify an attending doctor or nurse (hereafter "medical practitioner") if the parameters exceed a limit or are outside of a particular range. For example, if the patient monitor detects that the patient's blood pressure is too low or too high, it may generate a visual and/or audible alarm.

In most hospitals, a medical practitioner is responsible for several patients, many of whom may be in different rooms or wards. Accordingly, it is difficult or impossible for a single medical practitioner to be physically present at every patient monitor to notice the alarms. Simply broadcasting alarms among a group of networked patient monitors is not a complete solution. For example, the medical practitioner might not be aware that a remote patient monitor has malfunctioned or become disconnected and is no longer transmitting alarms. No solution currently exists for providing a medical practitioner with a complete view of the alarm status of remote patient monitors. These and other problems are addressed by the present disclosure.

In one embodiment, a local patient monitor may display a plurality of physiological parameters for a local patient. In addition, the local patient monitor may display a remote monitoring interface along with the local patient's physiological parameters. The remote monitoring interface may include a plurality of status icons respectively representing a plurality of remote patient monitors.

Each status icon may graphically indicate a remote monitoring status of a respective remote patient monitor. For example, one status icon may indicate an active connection exists between the local patient monitor and the corresponding remote patient monitor. Another status icon may indicate that alarm information is being blocked at the source by the corresponding remote patient monitor. Yet another status icon may indicate that no signal is being received by the corresponding remote patient monitor. Still another status icon may indicate that display of alarm information from a corresponding remote patient monitor is locked, i.e., cannot be blocked at the local patient monitor except by a person with particular access rights. As described in greater detail below, various combinations of the foregoing may be indicated by the status icons in the remote monitoring interface.

In one embodiment, the local patient monitor may receive alarm information from a first remote patient monitor indicating that one or more physiological parameters for a remote patient are outside of a determined range. The alarm information may include, for example, location information (e.g., bed or room number) for the remote patient, as well as an alarm condition (e.g., tachycardia) indicated by the one or more physiological parameters. The local patient monitor may display the alarm information within the remote monitoring interface, optionally overlaying some or all of the status icons.

In one embodiment, the displayed alarm information fills substantially all of the remote monitoring interface. However, in certain instances, the local patient monitor may receive alarm information from a second remote patient monitor, while it is displaying alarm information from the first remote patient monitor in the remote monitoring interface. In such a case, the remote monitoring interface may be divided between displaying the alarm information from the first and second patient monitors (e.g., each may fill substantially half of the remote monitoring interface). In the case of the local patient monitor receiving alarm information from a third patient monitor, the remote monitoring interface may be divided between displaying alarm information from the first, second, and third patient monitors (e.g., each may fill substantially a third of the remote monitoring interface).

In one configuration, the remote monitoring interface may display a notification that alarm information from more than a determined number of remote patient monitors (e.g., three or more) has been received, and may allow the user to selectively display alarm information that cannot be simultaneously displayed in the remote monitoring interface for space reasons. The remote monitoring interface may also display an indication of whether alarm information from the local patient monitor is being sent to one or more remote patient monitors.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail in order to avoid obscuring more important aspects of the disclosure.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer or other electronic device. Alternatively, the steps may be performed by hardware components that include specific logic for performing the steps or by a combination of hardware, software, and/or firmware.

Embodiments may also be provided as a computer program product including a computer-readable medium having stored thereon instructions that may be used to program a computer or other electronic device to perform the processes described herein. The computer-readable medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

Referring now to FIG. 1, there is shown a block diagram of a patient monitoring system 100 according to one embodiment. The patient monitoring system 100 may include a plurality of patient monitors 122, 124, 126, which analyze and display physiological parameters, such as pulse, temperature, respiration, blood pressure, blood oxygen, electrocardiogram, and the like. The patient monitors 122, 124, 126 may be configured to communicate with each other through a network 128, such as a hospital's local area network (LAN) or the Internet.

In certain embodiments, a patient monitor (e.g., patient monitor 122) may be connected to the network 128 through a docking station 130, 132. The docking station 130, 132 may allow the patient monitor 122 to be easily removed and transported between different locations in a hospital or other medical facility. In the example embodiment of FIG. 1, the patient monitor 122 may be configured to be selectively coupled with, and selectively decoupled from, any of the respective docking stations 130, 132.

For illustrative purposes, the patient monitor 122 is shown as being coupled to docking station 130. In certain embodiments, the docking stations 130, 132 provide the respective patient monitor 122 with power and/or a connection to the network 128. Accordingly, the docking station 130 is illustrated as including a power interface 133 and a network interface 134. The power interface 133 may be configured to convert an alternating current (AC) power signal to a direct current (DC) power signal and/or provide power signal conditioning for the coupled patient monitor 122. The network interface 134 may include, for example, an Ethernet communication controller to allow the coupled patient monitor 122 to communicate to the network 128 through the docking station 130. The network interface 134 may be associated with an identifying address, such as media access control (MAC) address.

In certain embodiments, the docking station 130 may also include a memory device 136. The memory device 136 may include non-volatile random access memory (RAM) that provides addressable storage and may be used in certain embodiments to store configuration data, historical patient parameter data, or the like.

The patient monitor 122, according to the example embodiment illustrated in FIG. 1, includes a processor 140, a display device 142, a memory device 144, a communication device 146, a power module 148, a parameter acquisition unit 150, a user interface unit 152, and an alarm unit 154. The processor 140 is configured to process patient data signals received through the parameter acquisition unit 150 and to display the patient data signals (e.g., as waveforms and/or numerical values) on the display device 142. The parameter acquisition unit 150 receives the patient data signals from one or more sensors attached to a patient (not shown). The parameter acquisition unit 150 may be configured to process the acquired patient data signals in cooperation with the processor 140. The patient monitor 122 may store the patient data signals in the memory device 144 along with other data. For example, the patient monitor 122 may store a current set of configuration settings in the memory device 144.

In one embodiment, the communication device 146 is configured to communicate with the network 128 through the network interface 134 of the docking station 130, or directly if no docking station 130 is available. For example, in certain embodiments, the communication device 146 may be configured to wirelessly communicate with the network 128 when the patient monitor 122 is not coupled to any of the docking stations 130, 132. As illustrated in FIG. 1, the patient monitor 124 automatically establishes a wireless communication link 156 with the network 128 as a user transports the patient monitor 124 between docking stations 130, 132.

The power module 148 receives a power signal from the power interface 133 of the docking station 130. The power module 148 provides any necessary power conversions and distributes power throughout the patient monitor 122. The power module 148 may include a battery that is charged through the power interface 133 while the patient monitor 122 is coupled to the docking station 130.

The user interface unit 152, in cooperation with the processor 140 and the display device 142, may be configured to process and format the acquired physiological parameters for display in a graphical user interface (GUI). As described in greater detail below, the user interface unit 152 may also be configured to display physiological parameters from another monitor via a remote monitoring interface (not shown).

The alarm unit 154 may be configured to generate audible and/or visual alarms when physiological parameters for a local patient are outside of a determined range. As described in greater detail below, the alarm unit 154 may also be configured to receive alarm information from one or more remote patient monitors. The alarm information may include, for example, location information for the remote patient and an alarm condition indicated by the one or more physiological parameters for a remote patient that are outside of a determined range. The alarm unit 154, in cooperation with the processor 140, display device 142, and user interface unit 152, may display the alarm information within the remote monitoring interface, as described hereafter.

An artisan will recognize from the disclosure herein that the parameter acquisition unit 150, user interface unit 152, and/or alarm unit 154 may be combined with the processor 140 into a single unit. Further, the processor 140, parameter acquisition unit 150, user interface unit 152, and/or alarm unit 154, either combined or separately, may include a special purpose processor configured to perform the processes described herein. In another embodiment, the processor 140, parameter acquisition unit 150, user interface unit 152, and/or alarm unit 154, either combined or separately, may include a general purpose processor configured to execute computer-executable instructions (e.g., stored in a computer-readable medium, such as the memory device 144) to perform the processes described herein.

Figure 2:
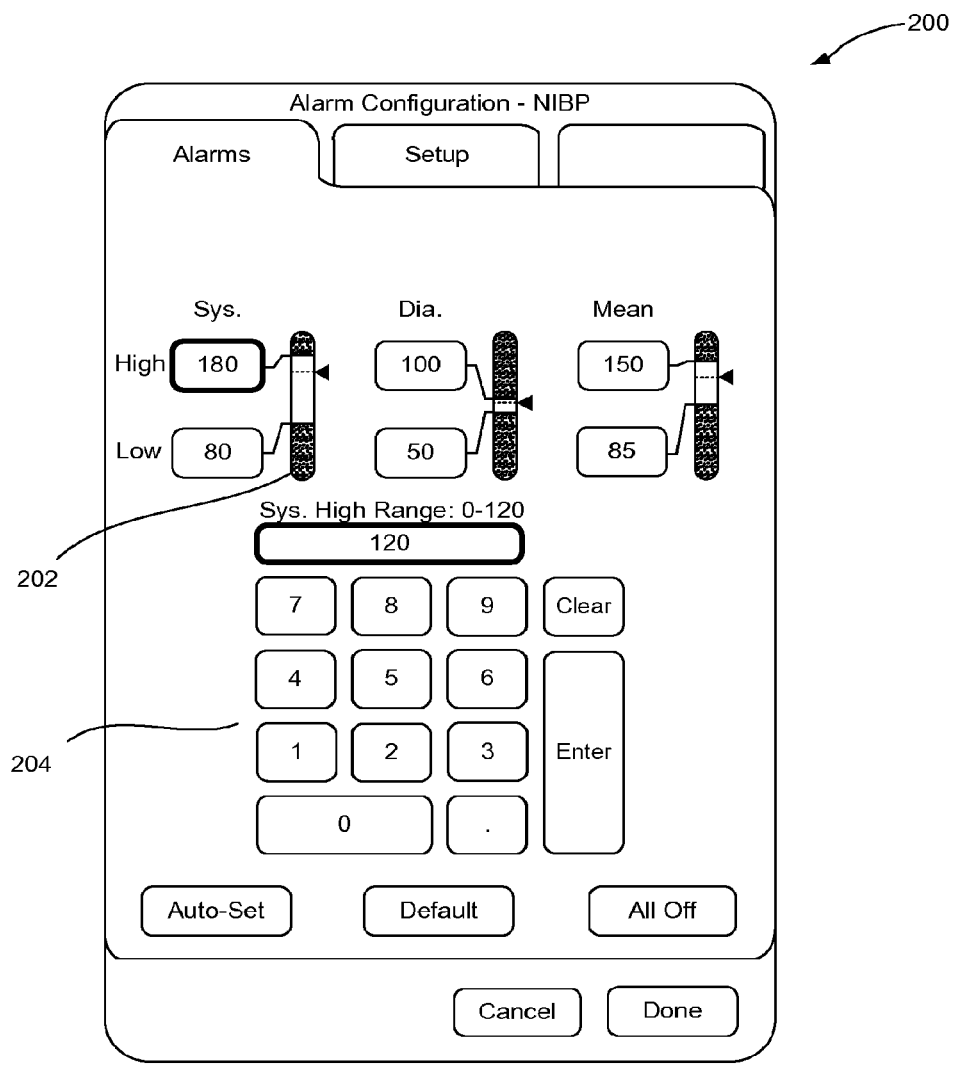
FIG. 2 graphically illustrates an alarm configuration interface according to one embodiment.

FIG. 2 illustrates an exemplary alarm configuration interface 200 for setting alarm conditions within a patient monitor, such as the patient monitor 122 of FIG. 1. In one embodiment, a medical practitioner may specify safe ranges for various physiological parameters, outside of which an alarm should be triggered. For instance, the user may specify that an alarm should be triggered if a patient's systolic pressure exceeds 180 or drops below 80, or if the patient's diastolic pressure is greater than 100 or less than 50. For certain parameters, the term "range" may be represented as a single value, such as an upper or lower limit. Some alarms may be triggered by a combination of parameters being within particular ranges and/or exceeding or being lower than particular thresholds.

In one embodiment, the alarm configuration interface 200 may include a visual representation of various controls or inputs, such as sliders 202 or keypads 204, for specifying safe and/or unsafe ranges for specified parameters. The range data may be stored, in one embodiment, in the memory device 144 shown in FIG. 1. The configuration of alarms typically occurs on the local patient monitor and each remote patient monitor.

Figure 3:
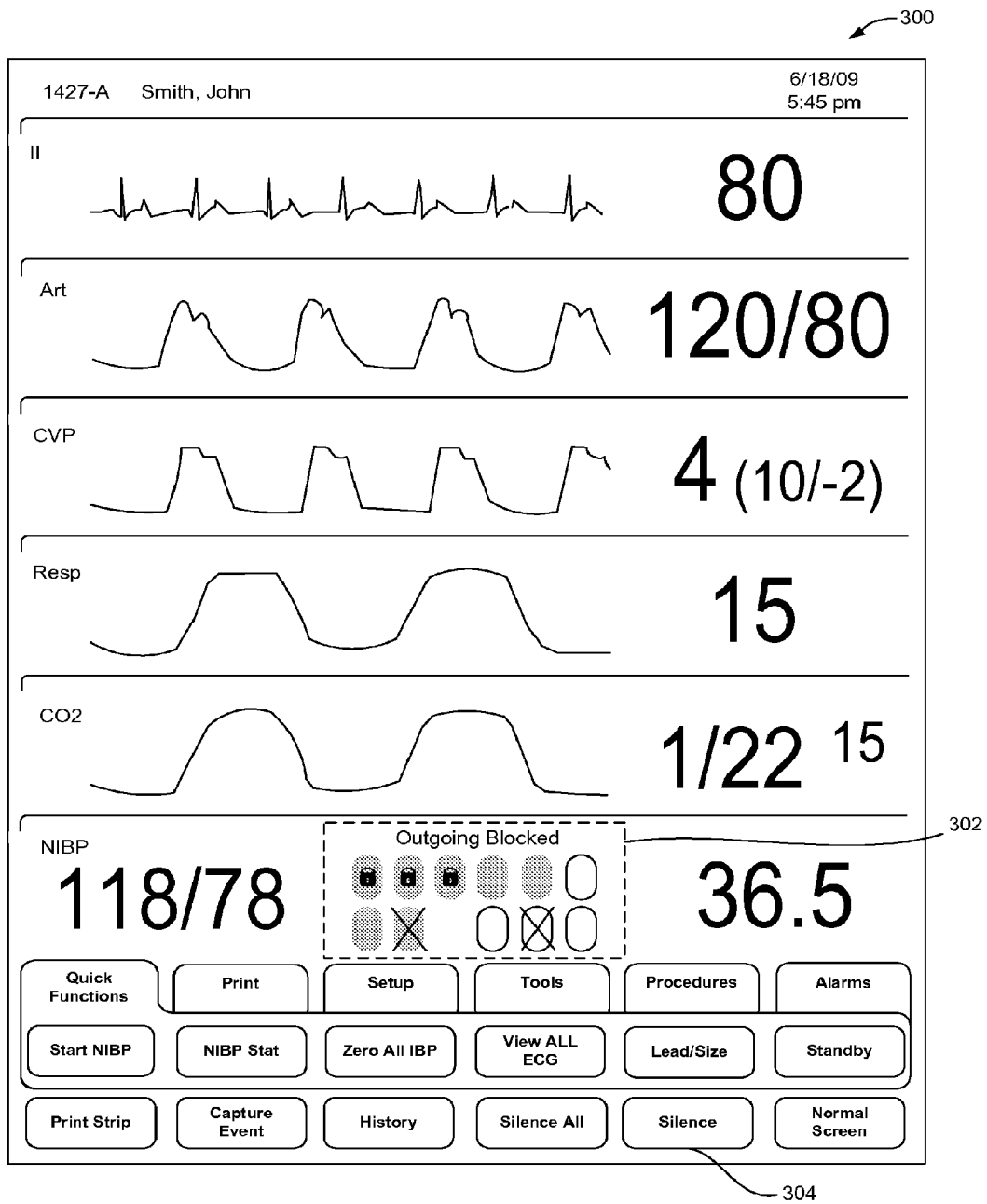
FIG. 3 graphically illustrates a patient parameter interface according to one embodiment.

FIG. 3 illustrates a patient parameter interface 300 according to one embodiment. The patient parameter interface 300 may display waveforms and/or numerical values for a plurality of physiological parameters acquired by the parameter acquisition unit 150 of FIG. 1.

As previously noted, a medical practitioner is typically responsible for multiple patients, many of whom may be in different rooms or wards. Accordingly, it is difficult or impossible for a single medical practitioner to be physically present at every patient monitor. Accordingly, in one embodiment, a local patient monitor, such as the patient monitor 122 of FIG. 1, may receive alarm information via the network 128 from a plurality of remote patient monitors 124, 126. The alarm information may include a location (e.g., bed or room number) of the patient, as well as an alarm condition (e.g., tachycardia) triggered by physiological parameters being monitored by the remote patient monitors 124, 126.

The local patient monitor 122 may also receive status information indicative of the remote monitoring status of each of the remote patient monitors 124, 126 accessible via the network 128. The alarm and status information may be displayed, in one embodiment, within a remote monitoring interface 302, which may be displayed with, or within, the patient parameter interface 300. In the illustrated embodiment, the remote monitoring interface 302 may be a region or "tile" within the patient parameter interface 300.

Figure 4:
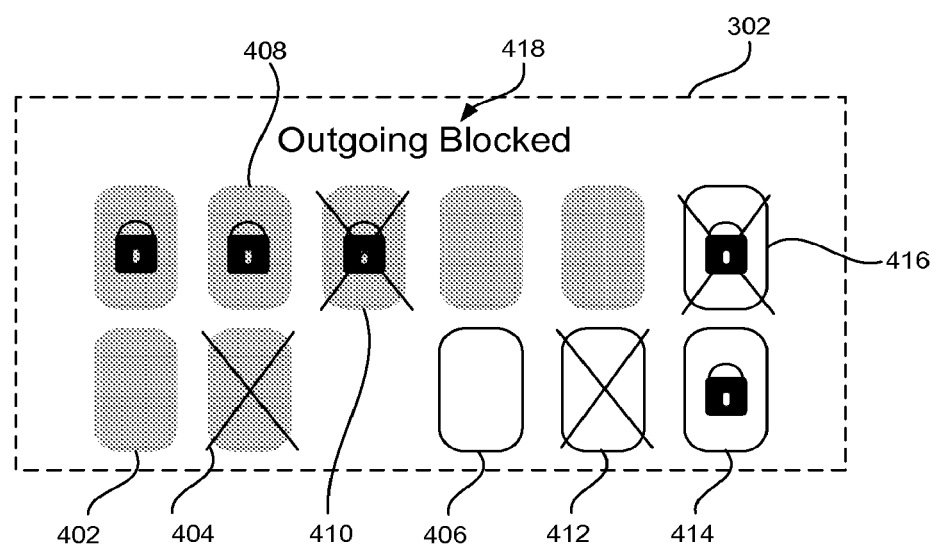
FIG. 4 graphically illustrates a remote monitoring interface according to one embodiment.

Referring to FIG. 4, in one operational mode, the remote monitoring interface 302 may display a plurality of status icons graphically indicating the remote monitoring status of a respective remote patient monitor. For example, one status icon 402 may indicate an active connection (communication link) exists between the local patient monitor and the corresponding remote patient monitor. In the example embodiment, the status icon 402 may be represented as a solid shape, such as a rounded rectangle, having a suitable color (e.g., green) to graphically indicate an active/non-alarm status.

Another status icon 404 may indicate that a connection between the local and remote patient monitor is active, but that alarm information is being blocked at the source by the remote patient monitor. This may occur, for example, when a medical practitioner needs to disconnect the sensors from a patient while performing tests. To avoid triggering an alarm, the medical practitioner may temporarily block outgoing alarms from the remote patient monitor. In one embodiment, the status icon 404 may be represented as an "X" that overlays one of the other status icons described in connection with FIG. 4.

Yet another status icon 406 may indicate that no signal is being received from the corresponding remote patient monitor. This may occur when the remote patient monitor has malfunctioned, has been accidentally or intentionally disconnected from the network, has been powered down, etc. The status icon 404 may be represented, in one embodiment, as an outline of the same shape as status icon 402.

Figure 5:
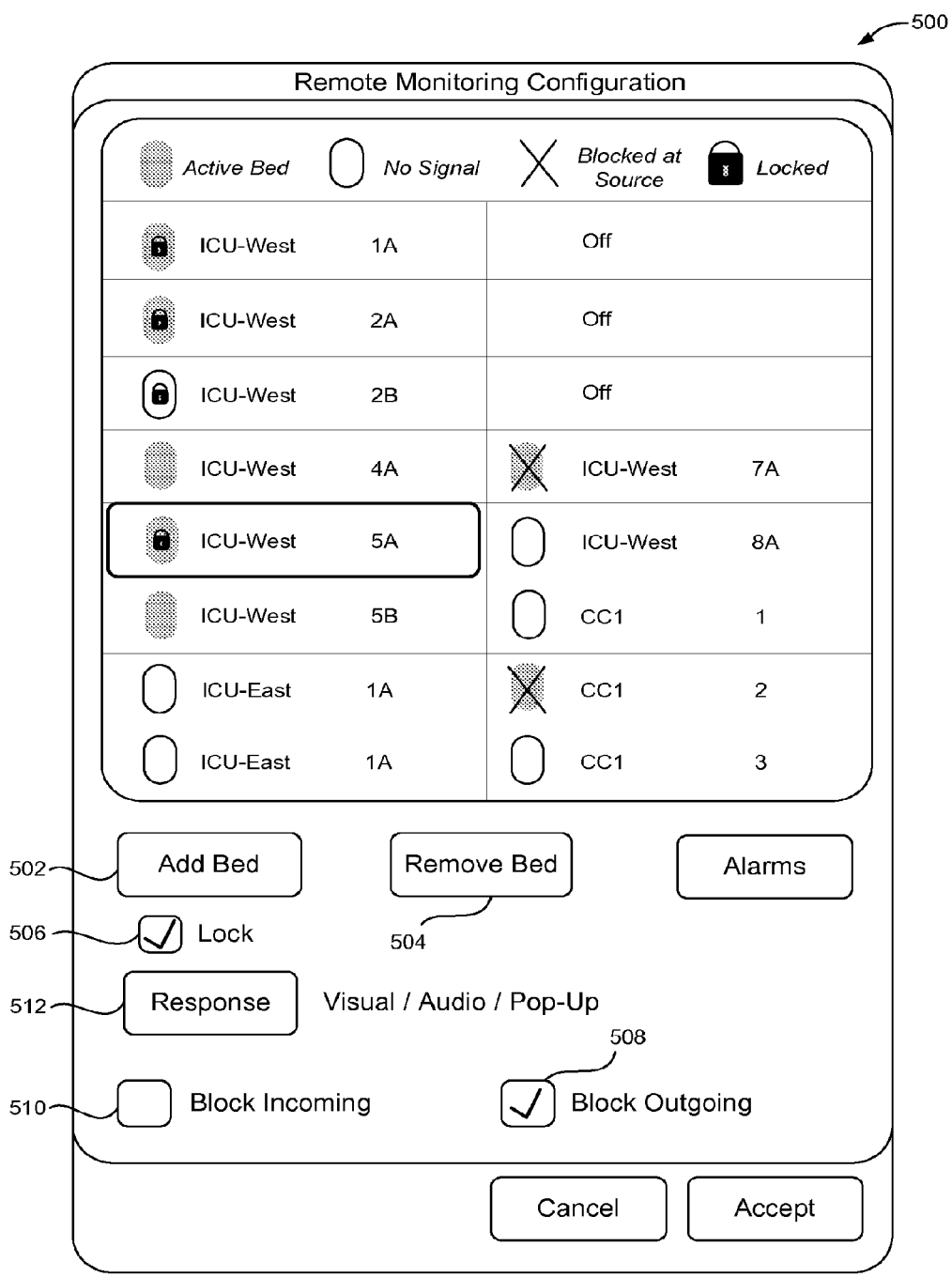
FIG. 5 graphically illustrates a remote monitoring configuration interface according to one embodiment.

Still another status icon 408 may indicate that the display of alarm information from a corresponding remote patient monitor cannot be blocked at the local patient monitor except by a person with particular access rights. Referring also to FIG. 5, there is shown a remote monitoring configuration interface 500 for allowing a medical practitioner to specify which remote patient monitors are to be represented within the remote monitoring interface 302 of FIG. 3. The remote monitoring configuration interface 500 may provide various controls, such as an "add bed" control 502, for adding a status icon representing a selected remote patient monitor, and a "remove bed" control 504 for removing a status icon representing a selected remote patient monitor. In one embodiment, alarm information for a remote patient monitor is only displayed when a corresponding status icon is shown within the remote monitoring interface 302.

In one embodiment, the ability to remove status icons from the remote monitoring interface 302 via the "remove bed" control 504 may be restricted based on access rights. For example, in some hospitals, a nurse supervisor may want to "lock" certain status icons, such that other medical practitioners cannot delete them from the remote monitoring interface 302. This may be accomplished, in one embodiment, by activating a "lock" button 506 in connection with the "add bed" button 502. In order to subsequently remove a "locked" status icon, a user may have to specify a password or otherwise establish sufficient access rights. Of course, various other methods and user interface controls may be used by a skilled artisan to accomplish similar purposes.

Referring again to FIG. 4, various combinations of the foregoing status icons may be provided in one embodiment. For example, one status icon 410 may indicate that an active connection exists between the local patient monitor and the corresponding remote patient monitor and that display of alarm information from the corresponding remote patient monitor cannot be blocked at the local patient monitor except by a person with particular access rights, but that alarm information is being blocked at the source.

Another status icon 412 may indicate that no signal is being received by a corresponding remote patient monitor and that alarm information is being blocked by the corresponding remote patient monitor. Still another status icon 414 may indicate that no signal is being received by a corresponding remote patient monitor and that display of alarm information from the corresponding remote patient monitor cannot be blocked at the local patient monitor except by a person with particular access rights. Yet another status icon 416 may indicate that no signal is being received by a corresponding remote patient monitor and that display of alarm information from the corresponding remote patient monitor cannot be blocked at the local patient monitor except by a person with particular access rights, but that alarm information is being blocked by the corresponding remote patient monitor.

In one embodiment, the remote monitoring interface 302 may display a message, icon, or other suitable indication 418 when alarm information from the local patient monitor is being blocked, i.e., is not being sent to one or more remote patient monitors. For example, in FIG. 4, the message "outgoing blocked" may be used for this purpose. In one embodiment, the remote monitoring configuration interface 500 of FIG. 5 may include a "block outgoing" button 508 to enable blocking of outgoing alarm information.

With continuing reference to FIG. 5, the remote monitoring configuration interface 500 may further include a "block incoming" button 510 to block incoming alarm information from one or more remote patient monitors. The remote monitoring configuration interface 500 may also include a "response" button 512 for tailoring how the alarm information from remote patient monitors is to be conveyed to the user of the local patient monitor. Various options may include pop-up windows, audible alerts, and/or a visual notification within the remote monitoring interface 300, as described in greater detail below.

Those of skill in the art will recognize that the remote monitoring interface disclosed above may present to a medical practitioner a complete view of the status of each patient monitor for which the medical practitioner is responsible. The medical practitioner can determine at a glance whether any of the patient monitors, for which he or she is responsible, is active, disconnected, blocked, or locked, or any combination of the foregoing. Thus, combined with the facility for displaying alarm information from the remote patient monitors, as detailed hereafter, the medical practitioner need not be physically present at each of the remote patient monitors in order to provide the requisite level of care for each patient.

Figure 6A:
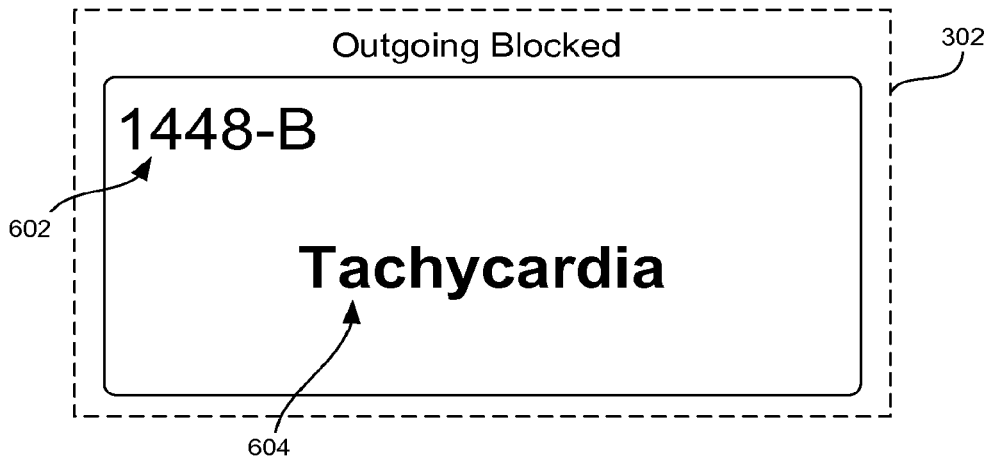
FIGS. 6A-6C graphically illustrate the remote monitoring interface of FIG. 4 displaying alarm information received from one or more remote patient monitors.

FIG. 6A illustrates one manner in which alarm information from a remote patient monitor may be displayed within the remote monitoring interface 302. In one embodiment, the local patient monitor may receive alarm information from a first remote patient monitor indicating that one or more physiological parameters for a remote patient are outside of a predetermined range. The alarm information may include, for example, location information 602 (e.g., bed or room number) for the remote patient and an alarm condition 604 (e.g., tachycardia) indicated by the one or more Physiological parameters.

As used herein, the location information 602 may include any indicator or reference to the patient, his or her physical location, and/or the patient monitor associated with the patient. The location information 602 might be represented, in one embodiment, by contextual information, such as position of an icon, rather than an explicit identifier.

In certain embodiments, the alarm condition 604 may be represented by an indication of severity rather than a specific medical condition. For instance, the alarm condition 604 may be color coded (e.g., red is most severe, white is least severe) based on different degrees of severity so that the medical practitioner can decide the level of response needed for the alarm condition 604.

Thus, a skilled artisan will recognize that references to "location" and "condition" in the disclosure and claims need not be limited to specific locations and specific conditions, but, rather, information that helps to locate the patient and information that helps to judge the severity of the condition and/or the level of response required.

The location information 602 and alarm condition 604 may be displayed within an icon that fills substantially all of remote monitoring interface, partially or completely overlaying the status icons of FIG. 4 in one embodiment. The icon may be displayed in a particular color (e.g., red) that contrasts the color (e.g., green) of the status icon 402 of FIG. 4. Display of the alarm information in the remote monitoring interface may be accompanied by other forms of visual or audible alerts to draw the medical practitioner's attention to the remote monitoring interface.

Figure 6B:
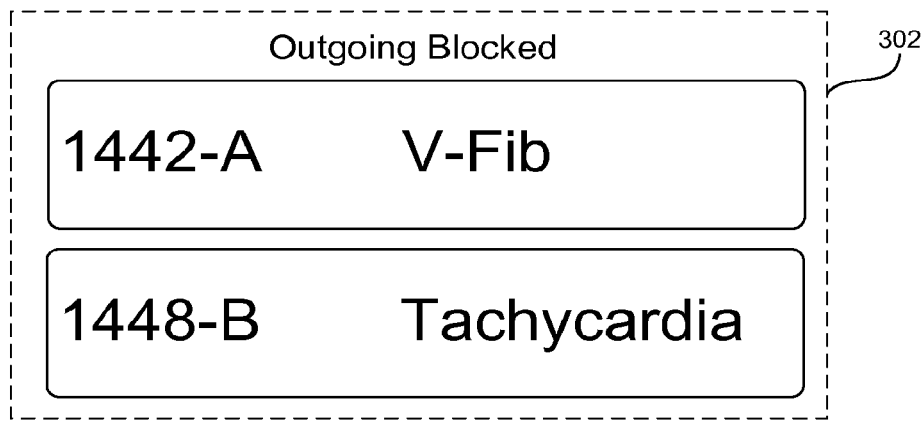

In certain instances, the local patient monitor may receive multiple sets of alarm information at approximately the same time or receive alarm information from a second remote patient monitor before an alarm triggered on a first patient monitor has been silenced. In such a case, as shown in FIG. 6B, the remote monitoring interface 302 may display both sets of alarm information, dividing itself between displaying the alarm information from the first and second patient monitors (e.g., each may fill substantially half of the remote monitoring interface 302). In the case of the local patient monitor receiving alarm information from a third patient monitor, the remote monitoring interface 302 may be divided between displaying alarm information from the first, second, and third patient monitors (e.g., each may fill substantially a third of the remote monitoring interface).

Figure 6C:
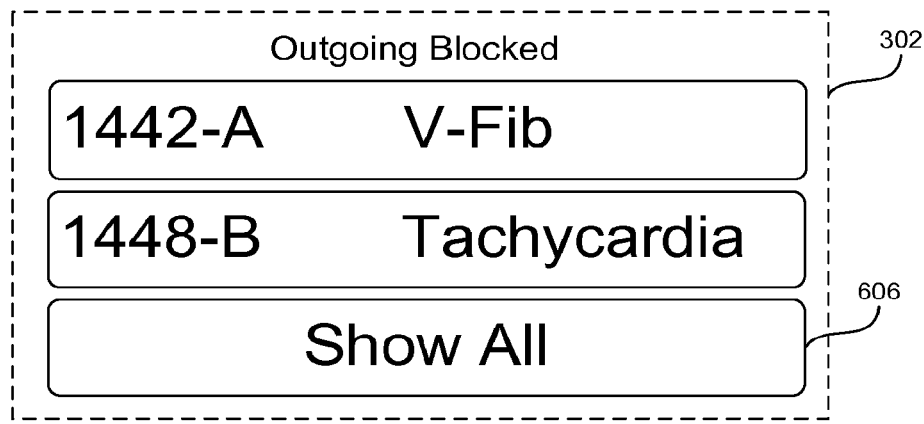

Depending on the size of the remote monitoring interface 302, it may be difficult to display more than two sets of alarm information. Accordingly, in one embodiment, as shown in FIG. 6C, a "show all" button 606 may be provided. In one embodiment, pressing the "show all" button 606 may enlarge the remote monitoring interface 302 to overlay a greater proportion of the patient parameter interface 300 of FIG. 3. In the embodiment of FIG. 3, the remote monitoring interface 302 is restricted to a small panel or "tile" within the patient parameter interface 300. Pressing the "show all" button 606 may cause all or some of the patient parameters and/or patient monitoring controls to be obscured by the alarm information.

In an alternative embodiment, when the number of concurrent sets of alarm information exceed a determined threshold, the remote monitoring interface 302 may cycle between different sets of alarm information in groups of two or more at a time with some additional indication (color, special icon, sound, etc.) informing the medical practitioner that not all sets of alarm information are being currently displayed.

Alarms may be silenced by a "silence" button 304 (shown in FIG. 3) or the like. In one embodiment, as alarms are silenced on the various remote patient monitors, the corresponding sets of alarm information may be removed from the remote monitoring interface 302. When all of the alarms have been silenced, the remote monitoring interface 302 may resume displaying the status icons, as illustrated in FIG. 3.

Figure 7:
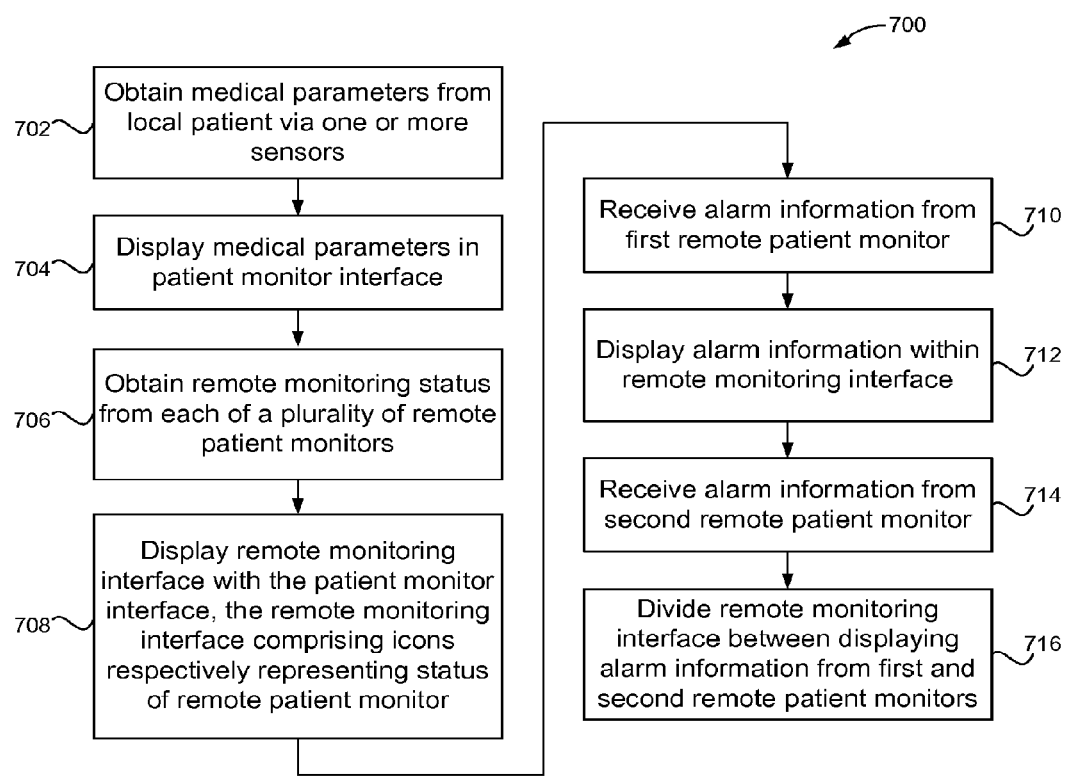
FIG. 7 is a flowchart of a method for remote patient monitoring according to one embodiment.

FIG. 7 is a flowchart of one embodiment of a method 700 for remote patient monitoring. At step 702, a local patient monitor may obtain physiological parameters from a local patient via one or more sensors. At step 704, the local patient monitor may display the physiological parameters in a patient parameter interface.

At step 706, the patient monitor may obtain a remote monitoring status from each of a plurality of remote patient monitors. At step 708, the patient monitor may display a remote monitoring interface with the local patient's physiological parameters. The remote monitoring interface may include icons respectively representing the remote monitoring status of a remote patient monitor.

At step 710, the patient monitor may receive alarm information from a first remote patient monitor indicating that one or more physiological parameters for a remote patient are outside of a determined range. The alarm information may include location information (e.g., bed or room number), as well as an indication of an alarm condition (e.g., tachycardia). At step 712, the patient monitor may display the alarm information within the remote monitoring interface.

At step 714, the patient monitor may receive alarm information from a second remote patient monitor. At step 716, the patient monitor may divide the remote monitoring interface between displaying alarm information for the first and second remote patient monitors.

Figure 8:
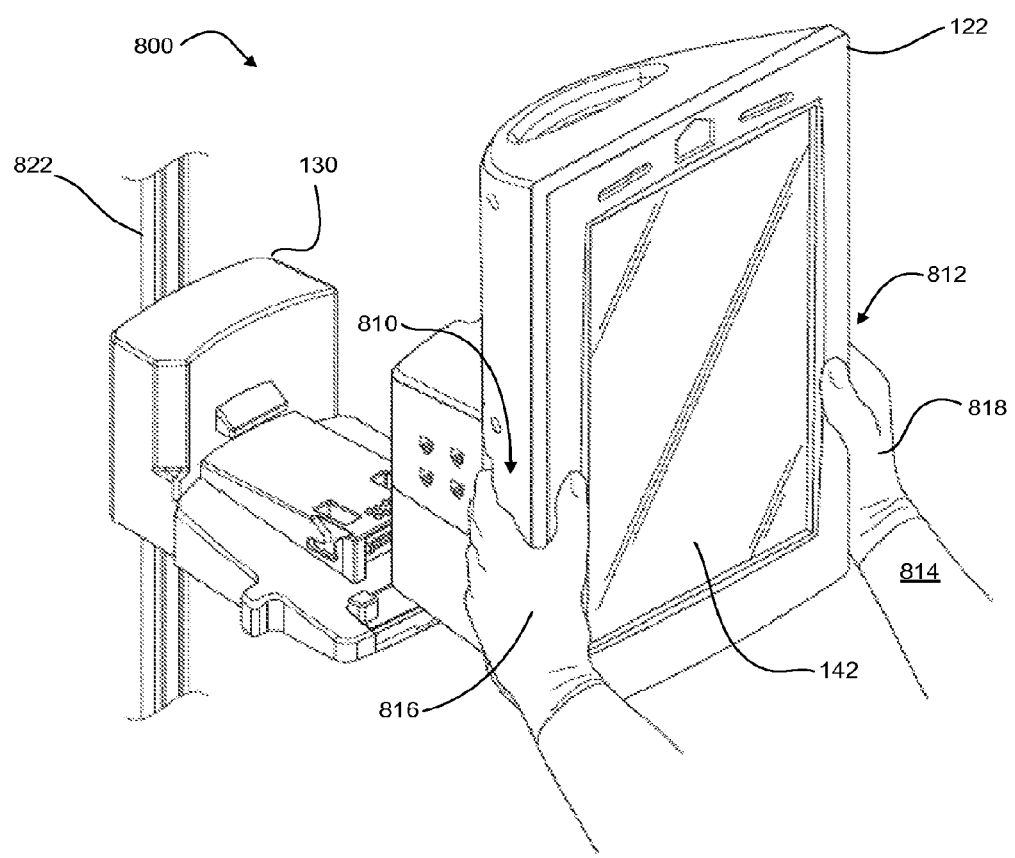
FIG. 8 is a perspective view of a patient monitoring system according to one embodiment.

FIG. 8 is a perspective view of a patient monitoring system 800 according to one embodiment. The embodiment shown in FIG. 8 is provided by way of example and an artisan will understand from the disclosure that any portable patient monitoring system may be used with the embodiments disclosed herein. The system 800 includes a patient monitor 122 and a docking station 130. The patient monitor 122 can be configured to selectively couple with and decouple from the docking station 130. The coupling between the patient monitor 122 and the docking station 130 can be mechanical, electrical, optical, and/or any other suitable variety. For example, the coupling can be for physical union, power transfer, and/or communication.

The patient monitor 122 may include one or more gripping regions 810, 812 that are configured to aid in coupling and decoupling the patient monitor 122 from the docking station 130. For example, a medical practitioner 814 can firmly grasp with his or her hands 816, 818 the gripping regions 810, 812 during removal of the patient monitor 122 from the docking station 130. When the patient monitor 122 is separated from the docking station 130, the full weight of the patient monitor 122 can be supported by a grip of the medical practitioner 814 on the gripping regions 810, 812.

The patient monitoring system 800 may include one or more actuators (not shown) which, when actuated, permit release of the patient monitor 122 from the docking station 130. The actuators can be integrated into the gripping regions 810, 812 or other portions of the patient monitor 122, so as to permit for convenient and continuous-movement dismounting of the patient monitor 122. For example, in some embodiments, a practitioner 814 can actuate an actuator using a hand 816, 818 while that hand 816, 818 is simultaneously holding a respective gripping region 810, 812.

In FIG. 8, the patient monitor 122 is illustrated as having been removed from the docking station 130. A front surface of the patient monitor 122 can include a display device 142 that is configured to display information in a visually perceivable format. The display device 142 may be of any suitable variety, including those presently known and those yet to be devised. For example, the display device 142 may include a liquid crystal display (LCD) panel. In some embodiments, the display device 142 may be configured to receive information or otherwise interact with a medical practitioner. For example, the display device 142 may include a touch screen.

In some embodiments, the display device 142 is configured to display information in a predetermined orientation that correlates with a docking orientation of the patient monitor 122. Information can be displayed on the display device 142 in an upright orientation when the patient monitor 122 is coupled with the docking station 130. For example, in the configuration depicted in FIG. 8, text, graphs, or other information can be displayed via the screen 142 in a "portrait" orientation that is natural for reading.

The patient monitor 122 may include one or more ports for receiving or delivering information, which can include one or more serial ports, USB ports, Ethernet ports, DVI ports, or any other suitable variety of ports, interfaces, or connectors. In some embodiments, information received via one or more of the ports can be displayed on the screen 142.

At least a portion of the information displayed by the patient monitor 122 may represent information received from a patient or that otherwise relates to the patient. For example, in some embodiments, one or more sensors (not shown) are connected to the patient to sense a particular parameter, and information obtained via the one or more sensors. The sensors may deliver information to the patient monitor 122 via one or more cables (not shown) connected to one or more ports.

The patient monitor 122 may be configured to both mechanically and electrically couple with the docking station 130. The patient monitor 122 may receive power from the docking station 130, which itself can receive power from a power source (not shown) via a power line or cord. The power source may include, for example, the AC wiring of a hospital.

The docking station 130 may be mounted in a substantially fixed position. For example, the docking station 130 may be rigidly mounted to a wall within a hospital room in a single position by one or more plates, brackets, screws, bolts, or other mounting hardware and attachment devices. As another example, the docking station 130 may be configured to transition among multiple fixed positions. For example, in the illustrated embodiment, the docking station 130 is coupled to a mounting strip 822, which is in turn mounted to a wall (not shown) of a hospital room. The docking station 130 is capable of being adjusted upward or downward along a path constrained by one or more channels defined by the mounting strip 822 so as to transition among a variety of positions. In each such position, the docking station 130 can be fixed relative to the mounting strip 822. In some embodiments, the docking station 130 is coupled with the mounting strip 822 via a mounting plate or a mounting bracket (not shown), the position of which can be adjusted upward or downward within the channels in any suitable manner.

In other embodiments, the docking station 130 may be secured to a hospital bed (not shown), a mechanical arm (not shown), or any other suitable object. In some embodiments, a bottom surface of the docking station 130 is positioned at a height of from about five feet to about six feet above a floor of a hospital room, so as to allow the patient monitor 122 to be viewed easily and/or to avoid interference with other objects in the room.

It will be understood by those having skill in the art that many changes may be made to the details of the above-described embodiments without departing from the underlying principles of the invention. The scope of the present invention should, therefore, be determined only by the following claims.

The invention claimed is:

1. A method comprising:
receiving, at a local patient monitor, a plurality of physiological parameters for a local patient from one or more local sensors;
displaying, on the local patient monitor, a patient monitoring interface with an upright orientation, the patient monitoring interface comprising a plurality of vertically aligned rectangular regions, wherein each rectangular region includes a parameter waveform and a numerical parameter value associated with the parameter waveform for one of the plurality of physiological parameters, wherein only a single number is displayed along with the parameter waveform in at least a same one of the rectangular regions, and wherein the numerical parameter value is the single number; and displaying, on the local patient monitor, a remote monitoring interface along with the patient monitoring interface, the remote monitoring interface for displaying alarm information for one or more of a plurality of remote patient monitors, wherein the remote monitoring interface is included in an additional rectangular region with a same width as each of the plurality of rectangular regions, and wherein the additional rectangular region is vertically aligned with the plurality of rectangular regions.

2. The method of claim 1, further comprising:

Receiving, at the local patient monitor, alarm information from a first remote patient monitor indicating that one or more physiological parameters for the first remote patient are outside of a determined range, the alarm information including location information for the remote patient and an alarm condition indicated by one or more physiological parameters for the first remote patient, and alarm information from a second remote patient monitor; and displaying the alarm information from the second remote patient monitor with the alarm information from the first patient monitor in the remote monitoring interface.

3. The method of claim 2, wherein the alarm information from the first remote patient monitor fills substantially all of remote monitoring interface.

4. The method of claim 2 further comprising:

dividing the remote monitoring interface between displaying the alarm information from the first and second remote patient monitors.

5. The method of claim 2, further comprising:

receiving third alarm information from a third remote patient monitor; and displaying the third alarm information with the first and second alarm information in the remote monitoring interface.

6. The method of claim 5, further comprising:

dividing the remote monitoring interface between displaying the alarm information from the first, second, and third remote patient monitors.

7. The method of claim 2, wherein the location information comprises an indication of a hospital bed.

8. The method of claim 1, further comprising displaying a status icon in the remote monitoring interface indicating a remote monitoring status for each remote patient monitor.

9. The method of claim 8, wherein at least one status icon indicates that an active connection exists between the local patient monitor and a corresponding remote patient monitor.

10. The method of claim 8, wherein at least one status icon indicates that alarm information is being blocked by a corresponding remote patient monitor.

11. The method of claim 8, wherein at least one status icon indicates that no signal is being received by a corresponding remote patient monitor.

12. The method of claim 8, wherein at least one status icon indicates that display of alarm information from a corresponding remote patient monitor cannot be blocked at the local patient monitor except by a person with particular access rights.

13. The method of claim 8, wherein at least one status icon indicates that an active connection exists between the local patient monitor and a corresponding remote patient monitor, but alarm information is being blocked by the corresponding remote patient monitor.

14. The method of claim 8, wherein at least one status icon indicates that an active connection exists between the local patient monitor and a corresponding remote patient monitor and that display of alarm information from the corresponding remote patient monitor cannot be blocked at the local patient monitor except by a person with particular access rights.

15. The method of claim 8, wherein at least one status icon indicates that an active connection exists between the local patient monitor and a corresponding remote patient monitor and that display of alarm information from the corresponding remote patient monitor cannot be blocked at the local patient monitor except by a person with particular access rights, but alarm information is being blocked by the corresponding remote patient monitor.

16. The method of claim 8, wherein least one remote monitoring status indicates no signal is being received by a corresponding remote patient monitor and that alarm information is being blocked by the corresponding remote patient monitor.

17. The method of claim 8, wherein least one remote monitoring status indicates no signal is being received by a corresponding remote patient monitor and that display of alarm information from the corresponding remote patient monitor cannot be blocked at the local patient monitor except by a person with particular access rights.

18. The method of claim 8, wherein least one remote monitoring status indicates no signal is being received by a corresponding remote patient monitor and that display of alarm information from the corresponding remote patient monitor cannot be blocked at the local patient monitor except by a person with particular access rights, but alarm information is being blocked by the corresponding remote patient monitor.

19. The method of claim 1, further comprising:

displaying within the remote monitoring interface an indication of whether alarm information from the local patient monitor is being sent to one or more remote patient monitors.

20. The method of claim 1, further comprising:

displaying a notification in the remote monitoring interface that alarm information from more than a determined number of remote patient monitors has been received.

21. The method of claim 20, wherein the notification comprise a button included in the remote monitoring interface.

22. The method of claim 21, wherein the button is displayed at the bottom of the remote monitoring interface.

23. The method of claim 21, wherein the button comprise a text of "show all".

24. The method of claim 1, wherein the remote monitoring interface is located below the patient monitoring interface all the time.

25. A patient monitoring system comprising:

a local patient monitor and a plurality of remote patient monitors, wherein the local patient monitor comprises:

a parameter acquisition unit configured to acquire physiological parameters from one or more local sensors for a local patient; and a user interface unit configured to display a patient monitoring interface with an upright orientation concurrently with a remote monitoring interface, the patient monitoring interface comprising a plurality of vertically-aligned rectangular regions, wherein each rectangular region includes a parameter waveform and a numerical parameter value associated with the parameter waveform for one of the physiological parameters, wherein only a single number is displayed along with the parameter waveform in at least a same one of the rectangular regions, wherein the numerical parameter value is the single number;

wherein the remote monitoring interface is included in an additional rectangular region with a same width as each of the plurality of rectangular regions, and wherein the additional rectangular region is vertically aligned with the plurality of rectangular regions.

26. The patient monitoring system of claim 25, further comprising an alarm unit configured to receive alarm information from a first remote patient monitor indicating that one or more physiological parameters for a remote patient are outside of a predetermined range, the alarm information including location information for the remote patient and an alarm condition indicated by the one or more physiological parameters, wherein the alarm unit is further configured to receive alarm information from a second remote patient monitor;

and wherein the user interface unit is further configured to displaying the alarm information from the second patient monitor with the alarm information from the first patient monitor in the remote monitoring interface.

27. The patient monitoring system of claim 26, wherein the alarm information from the first remote patient monitor fills substantially all of remote monitoring interface.

28. The patient monitoring system of claim 26 wherein the user interface unit is configured to divide the remote monitoring interface between displaying the alarm information from the first and second remote patient monitors.

29. The patient monitoring system of claim 26, wherein the alarm unit is further configured to receive alarm information from a third remote patient monitor; and wherein the user interface unit is further configured to display the third alarm information with the first and second alarm information in the remote monitoring interface.

30. The patient monitoring system of claim 29, wherein the user interface unit is further configured to divide the remote monitoring interface between displaying the alarm information from the first, second, and third remote patient monitors.

31. The patient monitoring system of claim 26, wherein the location information comprises an indication of a hospital bed.

32. The patient monitoring system of claim 25, wherein the wherein the user interface unit is further configured to display one or more status icons in the remote monitoring interface, each status icon in the remote monitoring interface indicating a remote monitoring status for a corresponding remote patient monitor.

33. The patient monitoring system of claim 25, wherein the user interface unit is to display within the remote monitoring interface an indication of whether alarm information from the local patient monitor is being sent to one or more remote patient monitors.

34. The patient monitoring system of claim 25, wherein the user interface unit is to display a notification in the remote monitoring interface that alarm information from more than a determined number of remote patient monitors has been received.

35. A computer-readable medium comprising program code for causing a computer to perform a method for remotely monitoring patients, the method comprising:

receiving, at a local patient monitor, a plurality of physiological parameters for a local patient from one or more local sensors;

displaying, on the local patient monitor, a patient monitoring interface with an upright orientation, the patient monitoring interface comprising a plurality of vertically aligned rectangular regions, wherein each rectangular region includes a parameter waveform and a numerical parameter value associated with the parameter waveform for one of the plurality of physiological parameters, wherein only a single number is displayed along with the parameter waveform in at least a same one of the rectangular regions, and wherein the numerical parameter value is the single number; and displaying, on the local patient monitor, a remote monitoring interface along with the patient monitoring interface, wherein the remote monitoring interface is included in an additional rectangular region with a same width as each of the plurality of rectangular regions, and wherein the additional rectangular region is vertically aligned with the plurality of rectangular regions.

* * * * *